United States Patent

Bonte et al.

[11] Patent Number: 5,807,555
[45] Date of Patent: Sep. 15, 1998

[54] **SKIN TREATMENTS WITH *SMELOPHYLLUM CAPENSE* EXTRACTS**

[75] Inventors: Frédéric Bonte, Courbevoie; Marc Dumas, Colombes; Catherine Lavaud, Tinqueux; Georges Massiot, Reims, all of France

[73] Assignee: LVMH Recherche, Nanterre, France

[21] Appl. No.: 849,453

[22] PCT Filed: Dec. 22, 1995

[86] PCT No.: PCT/FR95/01724

§ 371 Date: Jun. 18, 1997

§ 102(e) Date: Jun. 18, 1997

[87] PCT Pub. No.: WO96/20000

PCT Pub. Date: Jul. 4, 1996

[30] Foreign Application Priority Data

Dec. 23, 1994 [FR] France .................................. 94 15576

[51] Int. Cl.$^6$ .......................... A61K 35/78; A61K 31/70; A61K 31/375; C12N 5/00
[52] U.S. Cl. ....................... 424/195.1; 435/325; 435/357; 435/371; 435/390; 435/404; 514/23; 514/474; 514/844; 548/535; 562/562
[58] Field of Search .................... 424/195.1, 400; 514/844, 23, 474; 548/535; 562/562; 435/357, 371, 390, 404

[56] References Cited

PUBLICATIONS

Lavaud et al. Bull. Societe Royale des Sciences de Liege, vol. 63, pp. 455–463, 1994.

*Primary Examiner*—David M. Naff
*Assistant Examiner*—Janet M. Kerr
*Attorney, Agent, or Firm*—Dennison, Meserole, Pollack & Scheiner

[57] ABSTRACT

The present invention relates to a method and composition for topically administering a *Smelophyllum capense* extract as a cosmetic, dermatologic, or pharmaceutical composition to promote collagen synthesis. Administration of the composition results in the firming of the skin, improves healing and is suitable for treating various pathologies accompanied with a deficiency in collagen. The extract can also be added to cell culture medium used in the culture of skin cells, particularly skin fibroblasts. The composition can contain between 0.0001% and 1% by weight of the *Smelophyllum capense* extract, and the extract can be obtained by extraction with a polar solvent. The composition can contain other ingredients including ascorbic acid, madecassic acid, asiatic acid, madecassoside, asiaticoside, alpha-1-protease inhibitor, collagenase inhibitors, elastase inhibitors, lysine, proline, 2-oxoglutarate and ginsenoside Ro.

35 Claims, No Drawings

SKIN TREATMENTS WITH *SMELOPHYLLUM CAPENSE* EXTRACTS

BACKGROUND OF THE INVENTION

The present invention essentially relates to a cosmetic or pharmaceutical and particularly dermatological composition, and a culture medium containing a *Smelophyllum capense* extract.

More specifically, the present invention relates to the use of a *Smelophyllum capense* extract, for preparing a cosmetic or pharmaceutical and particularly dermatological composition, which particularly promotes collagen synthesis, and which is intended in particular for controlling the effects of skin ageing, for obtaining a skin firming, for improving healing or for treating the various pathologies accompanied with a deficiency of collagen; or as one of the active principles or additives for a cell or tissue culture medium, especially for the mass culture of skin cells, in particular fibroblasts, as well as cosmetic or pharmaceutical compositions or culture media comprising application thereof.

The *Smelophyllum capense* plant belongs to the Sapindaceae family which groups about 1,700 plant species. The plants of this family contain saponines which have been used for a long time as a detergent and as fish poison.

The *Smelophyllum capense* plant is a tree of relatively modest height, it being from 3 to 4 meters tall, that is found in the endemic state particularly in the forests of the southern part of South Africa (see R. B. Drumont, "Trees of Southern Africa, C. Struik Publisher, Capetown, 1984, page 531).

It has now been discovered that *Smelophyllum capense* extracts have a large interest in cosmetics, particularly for skin care.

In particular, a surprising activity of the *Smelophyllum capense* extracts has been discovered on the synthesis of collagen, in particular of type I collagen, hereinafter referred to as the abbreviation "collagen I". Now the skin essentially contains collagen I, a protein synthesised by the fibroblasts which are the major cells of the dermis. This protein plays a support role and is responsible for the rheological qualities of the dermis, in particular, it is responsible for its firmness and for the upkeep of its structure (E. U. KUCHARZ, "The collagens: Biochemistry and pathophysiology", Springer Verlag, Berlin 1992). Furthermore, it has been demonstrated that the fibroblasts of the dermis of elderly people secrete less collagen than those of young subjects (M. DUMAS et al, Mech, Ageing Dev. (1994) 73, 179–187). Thus, with age, a decrease of the rheological qualities, and a decrease in its response to constraints to which it is submitted very day is produced. The skin stretches, reacts less well to tensions, looses its tonus and wrinkles form.

From this, the action of *Smelophyllum capense* extracts upon the synthesis of collagen renders the extracts particularly useful for controlling the effects of skin ageing, such as wrinkles or the slackening of the tissues of the skin support, or for improving healing.

SUMMARY OF THE INVENTION

The principal aim of the present invention is to solve the new technical problem consisting of providing a novel formulation of a cosmetic or pharmaceutical and particularly dermatological composition which has a good effectiveness upon the prevention or the treatment of the effects of skin ageing, as well as upon the skin firming, or for improving healing.

Another principal aim of the present invention is to solve this novel technical problem in a particularly simple and satisfactory way which is useable on an industrial scale, particularly in the cosmetic or pharmaceutical industry.

Thus, according to a first aspect, the present invention relates to the use of a *Smelophyllum capense* extract as cosmetic agent, particularly for care of the skin.

DETAILED DESCRIPTION OF THE INVENTION

According to an embodiment variant of the invention, a *Smelophyllum capense* extract is used for preparing a cosmetic or pharmaceutical and particularly dermatological composition which particularly promotes collagen synthesis, in particular that of collagen I, and particularly intended for improving skin healing, for improving the biomechanical and the appearance of the surface of the skin, for obtaining a skin firming, for controlling the effects of skin ageing or for treating the various pathologies accompanied with a deficiency of collagen.

According to an advantageous embodiment variant, the *Smelophyllum capense* extract is used for preparing a composition with an anti-ageing effect on the skin, in particular anti-wrinkles, intended for preventing the appearance of wrinkles or for reducing wrinkle depth.

According to a particular embodiment variant, the aforementioned *Smelophyllum capense* extract is obtained by extraction with a polar solvent, such as a lower alcohol advantageously selected from methanol or an aqueous-ethanol mixture, preferably from the bark of the plant, preferably still from the bark of the root of this plant.

In particular, the *Smelophyllum capense* extract can be obtained according to the method described hereinafter as an indication and in no way as being limiting.

A first extraction from the bark, preferably from the bark of the root of the plant, is carried out with a polar solvent, advantageously selected from the group consisting of: water, alcohols having preferably 1 to 4 carbon atoms, chlorinated solvents having preferably 1 to 2 carbon atoms, organic esters having preferably 3 to 6 carbon atoms; or from a mixed solvent based on any mixture of the aforementioned solvents.

More preferably, the solvent of the first extraction is selected from the group consisting of: water, methanol, ethanol a methanol-water mixture or an ethanol-water mixture, chloroform, dichloromethane. More preferably still, water, methanol, ethanol or mixtures thereof.

The ratio of the bark to the extraction agent is not critical and will generally be between 1:5 and 1:20 parts by weight.

The extraction is generally carried out at temperatures between ambient temperature and the boiling point of the solvent used for the extraction.

Preferably, this first extraction is carried out under reflux under atmospheric pressure for a period of time between 2 and 4 hours. Further, it is advantageously preceded by a soaking in the cold for 2 to 4 hours in the solvent of extraction.

At the end of the extraction, the solvent phase containing the extract is filtered and then concentrated and/or evaporated to dryness under reduced pressure. A first crude *Smelophyllum capense* extract according to the invention is thus obtained. This crude extract can be purified according to various methods well-known to the person skilled in the art.

According to a second aspect, the present invention also relates to a cosmetic composition characterised in that it comprises, as active ingredient, a cosmetically effective amount of a *Smelophyllum capense* extract preferably dispersed in a cosmetically acceptable excipient.

According to a particular embodiment variant, this cosmetic composition promotes the synthesis of collagen, in particular that of collagen I, and is intended particularly for controlling the effects of skin ageing, or for obtaining a skin firming. Such a composition, for example, can advantageously be used as a composition for preventing the appearance of wrinkles or for reducing wrinkle depth.

According to a third aspect, the invention further relates to a pharmaceutical and particularly dermatological composition which promotes the synthesis of collagen, in particular that of collagen I, characterised in that it comprises, as active ingredient, a pharmaceutically effective amount of a *Smelophyllum capense* extract dispersed in a pharmaceutically acceptable excipient.

According to a particular embodiment, said composition is intended for improving skin healing or for treating the various pathologies accompanied with a deficiency of collagen.

According to a fourth aspect, the invention further covers a method of cosmetic or pharmaceutical and particularly dermatological treatment, characterised in that it comprises the application of a cosmetically or pharmaceutically effective amount, for a cosmetic or pharmaceutical treatment, of a *Smelophyllum capense* extract, in particular dispersed in a cosmetically or pharmaceutically acceptable excipient. The particularly advantageous cosmetic or pharmaceutical applications at present result from the preceding description as well as from the following description in relation with the Examples and the claims. The same applies regarding the concentration of the extract.

In one or the other of the preceding aspects, the *Smelophyllum capense* extract will preferably be used at a concentration between 0.0001% and 1% by weight compared to the total weight of the final composition. Preferably, this concentration is between 0.01% and 0.25% by weight compared to the total weight of the final composition.

Equally, in any one of the preceding aspects, the composition according to the invention preferably further contains an active substance selected from the group constituted of ascorbic acid, madecassic acid, asiatic acid, madecassoside, asiaticoside, alpha-1-protease inhibitor, collagenase inhibitors, such as retinoic acid, elastase inhibitors, lysine, proline, 2-oxoglutarate, and ginsenoside $R_0$.

According to a fifth aspect, the present invention also relates to the use of a *Smelophyllum capense* extract as one of the active principles or one of the additives for a culture medium of cells or of tissues, in particular for the mass culture of skin cells, in particular fibroblasts. Advantageously, this use relates to the preparation of an artificial skin or dermis.

Also under this aspect, the invention relates to a method of treating fibroblasts in culture with an effective concentration of a *Smelophyllum capense* extract in order to obtain a promotion of the synthesis of collagen, in particular that of collagen I.

Thus, within the context of this culture, for example for preparing artificial skin and in particular an artificial dermis, by cell culture according to the techniques well-known to the person skilled in the art, an artificial skin or dermis is obtained by virtue of the method of the invention of very good quality, particularly regarding the biomechanical properties.

According to a preferred implementation variant of the use of the culture method, the fibroblasts are treated with a *Smelophyllum capense* extract at a concentration at the moment of the culture between 0.3 μg/ml and 30 μg/ml of culture medium.

According to another advantageous variant, ascorbic acid or one of its derivatives can be added to the culture medium at a non-cytotoxic concentration, in particular between 0.001 mM and 0.5 mM.

According to yet another advantageous variant, one or more of the following substances may be added to the culture medium: L-glutamine, L-lysine, 5-hydroxy-L-lysine, L-proline and 4-hydroxy-L-proline, it being possible for each one of said substances to be present at a concentration between 2 and 10 mM.

Other aims, characteristics and advantages of the invention shall appear clear to the person skilled in the art from the following description made with reference to several actually preferred embodiments of the invention, as well as to the Examples that follow. In these Examples, all percentages are given by weight, unless otherwise stated.

EXAMPLE 1

Preparation of a Methanol Extract of the Root Bark of *Smelophyllum capense*

Powdered *Smelophyllum capense* root bark is prepared by grinding dried root bark of this plant which originates from South Africa. 200 g of this powder are then soaked for 2 hours in 2 liters of methanol. The whole is refluxed for 3 hours, and then left to cool and filtered on sintered glass. The filtrate is evaporated to dryness. The residue weighing 44.6 g is taken up into 350 ml of methanol. A precipitation is carried out by the addition of 1.75 l of diethyl ether to this solution before filtering. The precipitate is then dried over a solid dehydrating agent such as $P_2O_5$. About 27 g of this precipitate is then dialysed for 4 days against 270 ml of demineralised water, before lyophilising. 13.6 g of extract according to the invention, known as extract $I_1$, are obtained.

EXAMPLE 2

Demonstration of the Activity of a Methanol Extract of *Smelophyllum capense* Root Bark Prepared According to Example 1, Extract $I_1$, on the Synthesis of Collagen by Human Fibroblasts in Culture Fibroblast Culture Cultures of fibroblasts of the healthy adult dermis are effected by using the method by explants with the aid of a sample of facial skin obtained from a 60-year old woman during a face lift.

The fibroblasts are cultivated to confluence in an E199 (Gibco) medium supplemented with 2 mM of L-glutamine (Gibco) and 10% v/v of foetal calf serum (Gibco) at 37° C. in a humidified 5% $CO_2$ atmosphere. In order to measure the collagen content, the primary cultures in confluence are collected with a solution of 1% trypsin and 0.02% EDTA in a phosphate buffered saline solution (PBS) at pH 7.2 and the cells are then sown at a density of $10^4$ fibroblasts per well in 96-well microculture plates (Falcon) in the presence of the same culture medium as that described above.

24 hours after sowing, the medium is removed and replaced by a medium of the same composition as the medium described previously, except that it does not contain any serum and that 25 μM of L-ascorbic acid are added as the sodium salt. Further, this new medium contains or does not contain the product to be tested (extract $I_1$) according to a treated culture or a control culture. Incubation is then carried out for a further period of 48 hours at 37° C. The product to be tested (extract $I_1$) was dissolved in DMSO before the incorporation in the culture medium (the final concentration of DMSO in the medium is 0.1% v/v).

Viability of the Cells

At the end of the incubation period, the medium is removed and a viability test of MTT cells was carried out in accordance with the publication of Denizot F. et al. J. Immunol. Methods, (1986) 89, 271–277. The cells are incubated with 100 μl of a solution of tetrazolium salt at 0.5 mg/ml (3-[4,5-dimethylthiazol-2-yl]-2,5-diphenyltetrazolium bromide or MTT) in the E 199 medium without phenol red (Gibco) for 3 h at 37° C. Then, 100 μl of isopropanol are added to each well to dissolve the dark Formazan blue derivative formed by the living cells. The level of absorbance at 540 nm is measured.

Collagen Determination

The amount of type I collagen secreted by the cells in the medium without serum after 48 hours of incubation with the mixture or the individual component is determined by an ELISA test as described previously in the publication of Dumas M. et al., Mech. Ageing Dev. (1994) 73, 179–187, and that of Grimaud J. P. et al., in: Methods of Enzymatic Analysis (Bermeyer, H. U., ed.), VCH Publishers, Weinheim, (1986),186–201.

The incubation media without serum and the cells remaining homogenised by sonification in ice are combined and transferred into wells of an immunoplate in plastic (NUNC) for an incubation of 24 hours at +4° C. in order to allow the adherence of the secreted collagen. Protease inhibitors (ethyl maleimide, phenylmethylsulfonyl fluoride, ethylenediaminetetraacetate, each at a final concentration of 1 mM) are added during this period. The plates are then reinserted with the PBS. A similar washing step is effected after each plate treatment.

After 24 hours incubation at 4° C. with serum albumin to avoid a non-specific linking, rabbit anti-human type I collagen antibodies (Institut Pasteur, Lyon, France) are added over 1.5 h at 22° C. and the bound antibodies are made to react with goat anti-rabbit IgG conjugated with alkaline phosphatase (Interchim, Montluçon, France). The absorbance of para-nitrophenol formed from para-nitrophenylphosphate (Sigma) by the alkaline phosphatase is measured at 405 nm. The optical densities are converted into nanograms of collagen by using a standard curve established with purified human type I collagen (Institut Jacques Boy, France).

Statistics

The levels of collagen (mean±SD, standard deviation, n=6) are compared to those determined on the non-treated cells (medium+L-ascorbate+DMSO) by the Student's t test with p<0.05 as level of significance.

Results

The percentage promotion A of the collagen I synthesis is calculated by comparing the quantities of collagen I secreted in the control culture (not receiving any product to be tested) $C_o$ and in the treated cultures $C_t$, from the following formula:

$$A = \frac{C_t - C_O}{C_O} \times 100$$

The whole of the results are shown in Table I below.

TABLE I

| Cultures | % viability/ control | Collagen I secreted by the fibroblasts (ng/10000 cells/48 h) | % stimulation A | Significance |
|---|---|---|---|---|
| Control culture without product | 100 | 584 | 0 | |
| Product of the invention $I_1$ at 1 μg/ml | 102 (NS)* | 884 | +51 | S* |
| Product of the invention $I_1$ at 2.5 μg/ml | 92 (NS)* | 1 164 | +99 | S* |

*S = significant
NS = non-significant

An examination of Table I shows first of all that the level of viability of the cells in the treated cultures did not vary significantly compared to that of the control cultures. Extract $I_1$ is not therefore cytotoxic.

In this Table, the amounts of collagen I secreted by the fibroblasts are expressed in ng/10000 cells/48 h.

It will be seen from Table I that the methanol extract of *Smelophyllum capense* has produced a significant promoting activity of the synthesis of collagen I by the fibroblasts. It is known, particularly from the publication of Dumas M. et al., in: Mech. Ageing Dev. (1994) 73, 179–187, that the amount of collagen I decreases during skin ageing.

Thus, the *Smelophyllum capense* extract can be used for products intended for fighting skin ageing or which necessitates an increase in the local synthesis of collagen as is the case during a treatment of wrinkles, or for contributing to the improvement of skin healing.

Thus, the *Smelophyllum capense* extracts can advantageously be used by virtue of their property of promotion of the synthesis of collagen, as active agent, in the cosmetic or pharmaceutical, particularly dermatological compositions, such as defined previously.

Various formulations of cosmetic compositions are given below:

EXAMPLE 3

| Skin firming massage gel | |
|---|---|
| *Smelophyllum capense* root bark extract $I_1$ of Example 1 | 0.1 g |
| Ethanol | 25 g |
| Glycerine | 2 g |
| Propyleneglycol | 2 g |
| Carbopol 940 ® | 1.25 g |
| Aqueous excipient with preservative optionally perfumed | q.s.for. 100.00 g |

A part of the aqueous excipient is used with the Carbopol to separately prepare a gel, the other part of the aqueous excipient is used for mixing with the other components and the gel is added in the solution obtained so as to form a gelified composition forming the massage gel.

This massage gel composition can be used three times a week for two months on the breasts.

EXAMPLE 4

Body Care Lotion for skin firming

| | |
|---|---|
| Smelophyllum capense root bark extract $I_1$ of Example 1 | 0.5 g |
| Solubilising agent (Cremophor RH40 ®) | 2 g |
| Hyaluronic acid | 1 g |
| Aqueous excipient containing a preservative optionally perfumed | q.s.for. 100.00 g |

The extract is first of all dissolved in the solubilising agent, then is added in the aqueous excipient to which the hyaluronic acid is added.

The lotion obtained can be used in a cure for three weeks on the sensitive areas of slackening such as the stomach and the thighs.

Example 5
Anti-wrinkle Emulsion

| | |
|---|---|
| Smelophyllum capense root bark extract $I_1$ of Example 1 | 0.10 g |
| Perfumed emulsified excipient | q.s.for. 100.00 g |

Example 6
Healing composition

| | |
|---|---|
| Smelophyllum capense root bark extract $I_1$ according to Example 1 | 0.5 g |
| Emulsified excipient, water in oil type | q.s.for. 100.00 g |

EXAMPLE 7

Firming and embellishment cream

| | |
|---|---|
| Smelophyllum capense root bark extract $I_1$ of Example 1 | 0.05 g |
| Asiaticoside | 0.1 g |
| Ascorbyl phosphate (magnesium salt) | 0.05 g |
| Plant glycoceramides | 0.05 g |
| Vitamin A palmitate | 0.01 g |
| Preservatives | 0.05 g |
| Emulsified excipients | q.s.for. 100.00 g |

This cream, applied twice a day, restores the qualities of firmness and elasticity, as well as the properties of skin barrier and the vividness of a young skin.

We claim:

1. A cosmetic composition comprising a cosmetically effective amount of Smelophyllum capense extract as an active ingredient, dispersed in a cosmetically acceptable excipient.

2. The composition of claim 1, wherein the concentration of the Smelophyllum capense extract is in the range of 0.0001% and 1% by weight compared to the total weight of said composition.

3. The composition of claim 1, wherein the concentration of the Smelophyllum capense extract is in the range of 0.01% and 0.25% by weight compared to the total weight of said composition.

4. The composition of claim 1, wherein said Smelophyllum capense extract is obtained from the bark of the Smelophyllum capense plant.

5. The composition of claim 4, wherein said Smelophyllum capense extract is obtained from the bark of the root of the Smelophyllum capense plant.

6. The composition of claim 1, wherein said Smelophyllum capense extract is obtained by extraction with a polar solvent.

7. The composition of claim 6, wherein said polar solvent is a lower alcohol.

8. The composition of claim 6, wherein said polar solvent is selected from the group consisting of methanol and an aqueous-ethanol mixture.

9. The composition of claim 1, which further contains an active substance selected from the group consisting of ascorbic acid, madecassic acid, asiatic acid, madecassoside, asiaticoside, alpha-1-protease inhibitor, collagenase inhibitors, elastase inhibitors, lysine, proline, 2-oxoglutarate, and ginsenoside $R_0$.

10. A method of treating the skin of a human or animal with a cosmetic, comprising delivering to the skin a composition comprising a cosmetically effective amount of a Smelophyllum capense extract dispersed in a cosmetically acceptable excipient.

11. The method of claim 10, wherein the Smelophyllum capense extract is present at a concentration in the range of 0.0001% to 1% by weight, compared to the total weight of said composition.

12. The method of claim 10, wherein the Smelophyllum capense extract is present at a concentration in the range of 0.01% to 0.25% by weight, compared to the total weight of said composition.

13. The method of claim 10, wherein the cosmetic is selected from the group consisting of promoting the synthesis of collagen, improving skin healing, controlling the effects of skin aging, preventing the appearance of wrinkles, reducing wrinkle depth, and obtaining skin firming.

14. The method of claim 13, wherein the cosmetic treatment consists of promoting the synthesis of collagen, wherein the collagen is collagen type I.

15. A pharmaceutical composition comprising a pharmaceutically effective amount of Smelophyllum capense extract as an active ingredient, dispersed in a pharmaceutically acceptable excipient.

16. The composition of claim 15, wherein the concentration of the Smelophyllum capense extract is in the range of 0.0001% and 1% by weight compared to the total weight of said composition.

17. The composition of claim 15, wherein the concentration of the Smelophyllum capense extract is in the range of 0.01% and 0.25% by weight compared to the total weight of said composition.

18. The composition of claim 15, wherein said Smelophyllum capense extract is obtained from the bark of the Smelophyllum capense plant.

19. The composition of claim 18, wherein said Smelophyllum capense extract is obtained from the bark of the root of the Smelophyllum capense plant.

20. The composition of claim 15, wherein said Smelophyllum capense extract is obtained by extraction with a polar solvent.

21. The composition of claim 20, wherein said polar solvent is a lower alcohol.

22. The composition of claim 20, wherein said polar solvent is selected from the group consisting of methanol and an aqueous-ethanol mixture.

23. The composition of claim 15, which further contains an active substance selected from the group consisting of ascorbic acid, madecassic acid, asiatic acid, madecassoside, asiaticoside, alpha-1-protease inhibitor, collagenase inhibitors, elastase inhibitors, lysine, proline, 2-oxoglutarate, and ginsenoside $R_0$.

24. A method of treating the skin of a human or animal with a pharmaceutical, comprising delivering to the skin of the human or animal a composition comprising a pharmaceutically effective amount, of a Smelophyllum capense extract dispersed in a pharmaceutically acceptable excipient.

25. The method of claim 24, wherein the *Smelophyllum capense* extract is present at a concentration in the range of 0.0001% to 1% by weight, compared to the total weight of said composition.

26. The method of claim 24, wherein the *Smelophyllum capense* extract is present at a concentration in the range of 0.01% to 0.25% by weight, compared to the total weight of said composition.

27. The method of claim 24, wherein the pharmaceutical treatment is selected from the group consisting of promoting the synthesis of collagen, improving skin healing, controlling the effects of skin aging, preventing the appearance of wrinkles, reducing wrinkle depth, and obtaining skin firming.

28. The method of claim 27, wherein the pharmaceutical treatment consists of promoting the synthesis of collagen, wherein the collagen is collagen type I.

29. A method of mass culturing fibroblast skin cells comprising adding to a fibroblast skin cell culture medium a *Smelophyllum capense* extract as an active principle in an amount effective to promote the synthesis of collagen by said fibroblast skin cells.

30. The method of claim 29, wherein the concentration of the *Smelophyllum capense* extract is in the range of 0.3 µg/ml to 30 µg/ml of culture medium.

31. The method of claim 29, wherein the collagen is collagen type I.

32. The method of claim 29, wherein ascorbic acid or a derivative of ascorbic acid is added to the culture medium at a non-cytotoxic concentration in the range of 0.001 mM to 0.4 mM.

33. The method of claim 29, additionally comprising adding to the culture medium at least one substance selected from the group consisting of L-glutamine, L-lysine, 5-hydroxy-L-lysine, L-proline and 4-hydroxy-L-proline, each added substance being present at a concentration between 2 mM and 10 mM.

34. A culture medium comprising fibroblast skin cells and an effective amount of *Smelophyllum capense* extract to promote the synthesis of collagen by said fibroblast skin cells.

35. The medium of claim 34, wherein the *Smelophyllum capense* extract is present at a concentration in the range of 0.3 µg/ml to 30 µg/ml of culture medium.

* * * * *